United States Patent
Takahashi et al.

(10) Patent No.: US 12,274,487 B2
(45) Date of Patent: *Apr. 15, 2025

(54) MEDICAL DEVICE

(71) Applicant: TERUMO KABUSHIKI KAISHA, Tokyo (JP)

(72) Inventors: Yusuke Takahashi, Hadano (JP); Yukitoshi Kato, Hadano (JP); Tomoaki Takemura, Kawasaki (JP); Nozomu Yamazaki, Hadano (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 1177 days.

This patent is subject to a terminal disclaimer.

(21) Appl. No.: 17/034,078

(22) Filed: Sep. 28, 2020

(65) Prior Publication Data
US 2021/0007791 A1 Jan. 14, 2021

Related U.S. Application Data

(63) Continuation of application No. PCT/JP2019/012690, filed on Mar. 26, 2019.

(30) Foreign Application Priority Data

Mar. 29, 2018 (JP) ................ 2018-064008

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1206* (2013.01); *A61B 2018/00214* (2013.01);
(Continued)

(58) Field of Classification Search
CPC ................ A61B 18/14; A61B 18/1206; A61B 2018/00214; A61B 2018/1253;
(Continued)

(56) References Cited

U.S. PATENT DOCUMENTS 5,853,422 A * 12/1998 Huebsch ............ A61B 17/0057
606/213
5,957,920 A * 9/1999 Baker ................ A61B 18/1485
607/101
(Continued)

FOREIGN PATENT DOCUMENTS

JP 2009512521 A 3/2009
JP 2012050538 A 3/2012
(Continued)

OTHER PUBLICATIONS

International Search Report (PCT/ISA/210) and translation and Written Opinion (PCT/ISA/237) mailed on May 14, 2019, by the Japanese Patent Office as the International Searching Authority for International Application No. PCT/JP2019/012690.
English Translations of the International Search Report (Form PCT/ISA/210) and the Written Opinion of the International Searching Authority (Form PCT/ISA/237) issued May 14, 2019, by the Japanese Patent Office in corresponding International Application No. PCT/JP2019/012690. (9 pages).
(Continued)

*Primary Examiner* — Linda C Dvorak
*Assistant Examiner* — Lindsay Regan Lancaster
(74) *Attorney, Agent, or Firm* — Buchanan Ingersoll & Rooney PC

(57) ABSTRACT

A medical device is disclosed which can suppress torsion of a wire in a circumferential direction in an expansion body formed using the wire. The medical device includes an elongated shaft portion, and an expansion body disposed in a distal portion of the shaft portion, the expansion body configured to expand and contract in a radial direction. The expansion body has wire portions in which a distal portion and a proximal portion are linked with the shaft portion, and a holding portion formed using at least one of the wire
(Continued)

portions, and holding a biological tissue. At least one of a proximal side and a distal side of the holding portion has an opening portion formed using a wire portion or formed using a plurality of the wire portions. When the expansion body expands, the wire portion forming the holding portion faces the opening portion.

20 Claims, 9 Drawing Sheets

(52) U.S. Cl.
CPC . *A61B 2018/1253* (2013.01); *A61B 2018/126* (2013.01); *A61B 2018/1467* (2013.01)

(58) Field of Classification Search
CPC ...... A61B 2018/126; A61B 2018/1467; A61B 18/06; A61B 18/082; A61B 2018/00267; A61B 2018/00351; A61B 2018/00357; A61B 2018/00595; A61B 2018/0212; A61B 18/1492; A61B 17/00; A61B 18/18; A61B 18/20
See application file for complete search history.

(56) References Cited

U.S. PATENT DOCUMENTS

| 8,882,697 | B2 | 11/2014 | Celermajer et al. | |
|---|---|---|---|---|
| 11,950,836 | B2* | 4/2024 | Takahashi | A61B 18/1492 |
| 2002/0082614 | A1 | 6/2002 | Logan et al. | |
| 2007/0118176 | A1 | 5/2007 | Opolski et al. | |
| 2008/0097422 | A1* | 4/2008 | Edwards | A61B 18/1492 606/34 |
| 2015/0011991 | A1* | 1/2015 | Buysman | A61B 18/1492 606/41 |
| 2020/0138445 | A1 | 5/2020 | Takahashi et al. | |

FOREIGN PATENT DOCUMENTS

| WO | 2009/055651 A1 | 4/2009 |
|---|---|---|
| WO | 2016/014821 A1 | 1/2016 |
| WO | 2019/009254 A1 | 1/2019 |

OTHER PUBLICATIONS

The extended European Search Report issued May 4, 2021, by the European Patent Office in corresponding European Patent Application No. 19776229.7-1113. (9 pages).

\* cited by examiner

FIG. 3
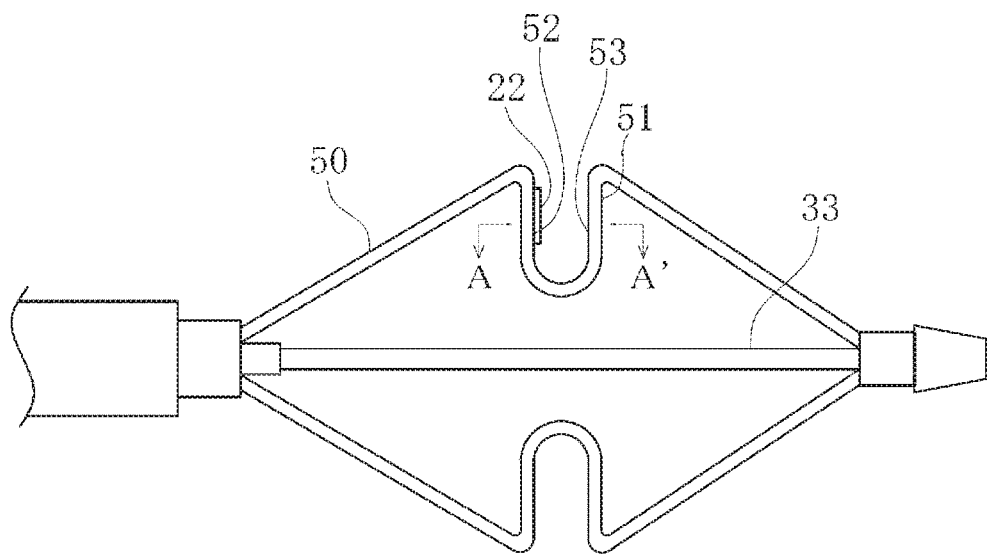
FIG. 4A
FIG. 4B
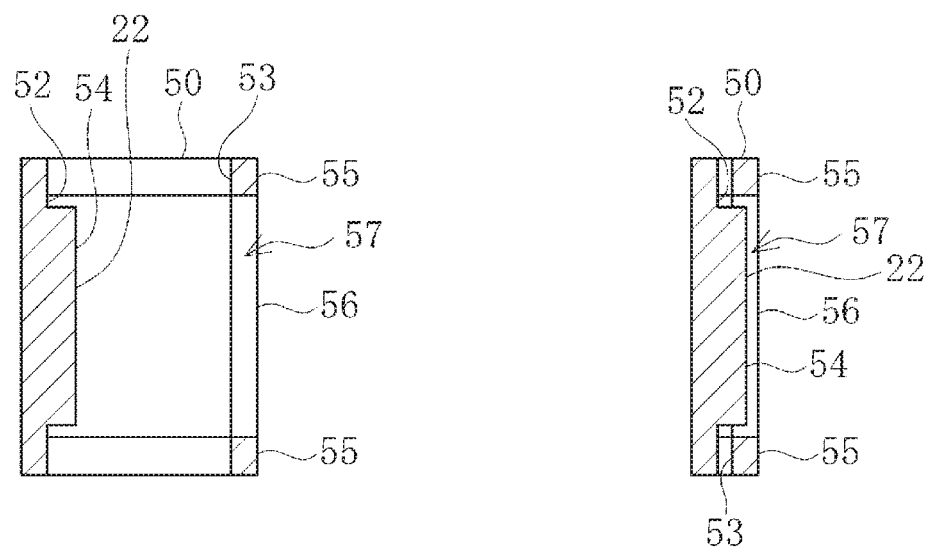

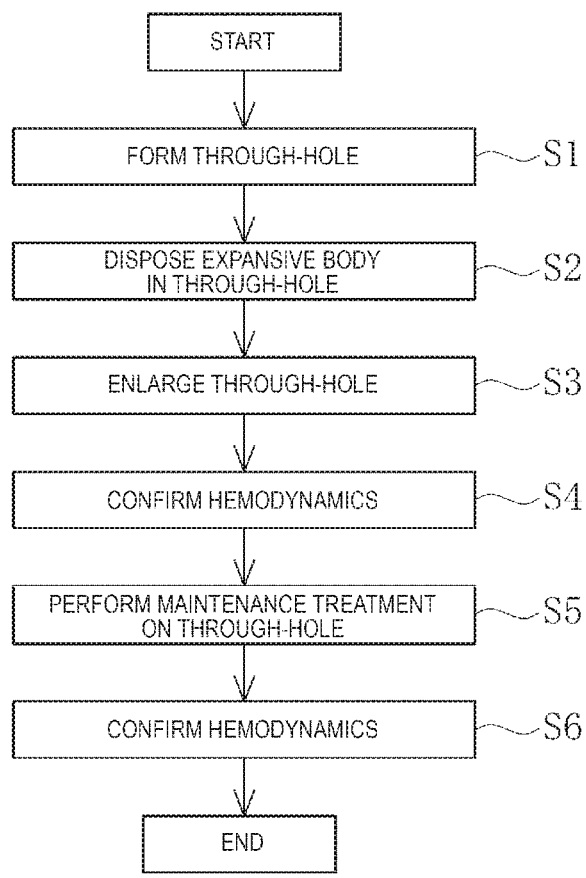

MEDICAL DEVICE

CROSS-REFERENCES TO RELATED APPLICATIONS

This application is a continuation of International Application No. PCT/JP2019/012690 filed on Mar. 26, 2019, which claims priority to Japanese Application No. 2018-064008 filed on Mar. 29, 2018, the entire content of both of which is incorporated herein by reference.

FIELD

The present disclosure generally relates to a medical device including a maintenance treatment element which applies energy to a biological tissue.

BACKGROUND DISCUSSION

Chronic heart failure is a known heart disease. Chronic heart failure is broadly classified into a systolic heart failure and a diastolic heart failure, based on a cardiac function index. In a patient suffering from the diastolic heart failure, myocardial hypertrophy appears, and stiffness (hardness) increases. Consequently, blood pressure increases in a left atrium, and a cardiac pumping function is degraded. In this manner, the patient may show heart failure symptoms such as a pulmonary edema. In addition, there is another heart disease of a patient who shows the following heart failure symptom. Due to pulmonary hypertension, blood pressure increases on a right atrium side, and the cardiac pumping function is degraded.

In recent years, shunt treatments have attracted attention. For the patients who suffer from heart failure, a shunt (through-hole) serving as an escape route for increased atrial pressure is formed in an atrial septum, thereby enabling heart failure symptoms to be alleviated. In the shunt treatment, the atrial septum is accessed using an intravenous approaching method, and the through-hole is formed to have a desired size. For example, a medical device disclosed in U.S. Pat. No. 8,882,697 is used as one of medical devices for performing the shunt treatment on the atrial septum.

According to the medical device disclosed in U.S. Pat. No. 8,882,697, a shunt hole is enlarged using a balloon serving as an expansion body disposed in a distal portion of a shaft portion, and the shunt hole is maintained by an electrode disposed in the balloon. However, when the through-hole is enlarged, the medical device blocks the through-hole with the balloon. Accordingly, hemodynamics cannot be confirmed. Therefore, the hemodynamics are confirmed after the balloon is removed, and thus, a therapeutic effect obtained by the through-hole cannot be immediately confirmed.

In order to confirm the hemodynamics when the through-hole is enlarged, it is conceivable that the expansion body is formed using wires to enable blood to flow from a space between the wires of the expansion body. However, in a case where the expansion body are formed using the wires, the wires may have torsion in a circumferential direction when the expansion body expands, thereby causing a possibility that an expansion force may not be sufficiently transmitted to a biological tissue.

SUMMARY

A medical device is disclosed, which can suppress torsion of wires in a circumferential direction in an expansion body formed using the wires.

In accordance with an aspect, a medical device is disclosed, which includes an elongated shaft portion, and an expansion body disposed in a distal portion of the shaft portion, the expansion body configured to expand and contract in a radial direction. The expansion body has a plurality of wire portions linked with the shaft portion, and a holding portion formed using at least one of the wire portions. At least one of a proximal side and a distal side of the holding portions has an opening portion formed in the wire portion or formed using two or more of the plurality of wire portions. When the expansion body expands, the wire portion forming the holding portion faces the opening portion.

In accordance with another aspect, a medical device is disclosed, which includes an elongated shaft portion, and an expansion body disposed in a distal portion of the shaft portion, the expansion body configured to expand and contract in a radial direction. The expansion body has a plurality of wire portions linked with the shaft portion, and a proximal side holding portion and a distal side holding portion which are formed using at least one of the wire portions. When the expansion body expands, the proximal side holding portion and the distal side holding portion are fitted together, or are alternately located in a circumferential direction.

In accordance with an aspect, a treatment method is disclosed for enlarging a through-hole of a biological tissue by using a medical device having an expansion body configured to expand and contract in a radial direction, the method comprising: positioning a holding portion of the expansion body in the through-hole of the biological tissue, the expansion body including a plurality of wire portions linked with the shaft portion, and the holding portion formed using at least one of the plurality of wire portions, and at least one of a proximal side and a distal side of the holding portion includes an opening portion formed in a wire portion or formed using two or more of the plurality of wire portions; causing the holding portion to face the opening portion and to further hold the biological tissue from both sides of the through-hole; enlarging a diameter of the through-hole by expanding the expansion body; and performing a maintenance treatment by using a maintenance treatment element of the holding portion.

In the medical device configured as described above, an uneven structure is formed in which at least one of the proximal side and the distal side of the holding portion can enter the opening portion formed in the other. The uneven structure suppresses positional displacement in the circumferential direction when the biological tissue is held by the holding portion, and suppresses torsion (i.e., twisting) of the expansion body in the circumferential direction. Therefore, an expansion force can be reliably transmitted to the biological tissue.

In addition, in the medical device configured as described above, the proximal side holding portion and the distal side holding portion have a relationship in which both of these are fitted together or alternately located in the circumferential direction. In this manner, the uneven structure is formed. The uneven structure suppresses the positional displacement in the circumferential direction when the biological tissue is held by the proximal side holding portion and the distal side holding portion, and suppresses the torsion of the expansion body in the circumferential direction. Therefore, the expansion force can be reliably transmitted to the biological tissue.

BRIEF DESCRIPTION OF THE DRAWINGS

FIG. 3 is an enlarged front view illustrating the vicinity of the expansion body.

FIG. 4A is a sectional view taken along line A-A' in FIG. 3, and FIG. 4B is a view for describing a states before and after a proximal side holding portion enters an opening portion.

FIG. 6 is a flowchart of a treatment method using the medical device.

DETAILED DESCRIPTION

Figure 1:
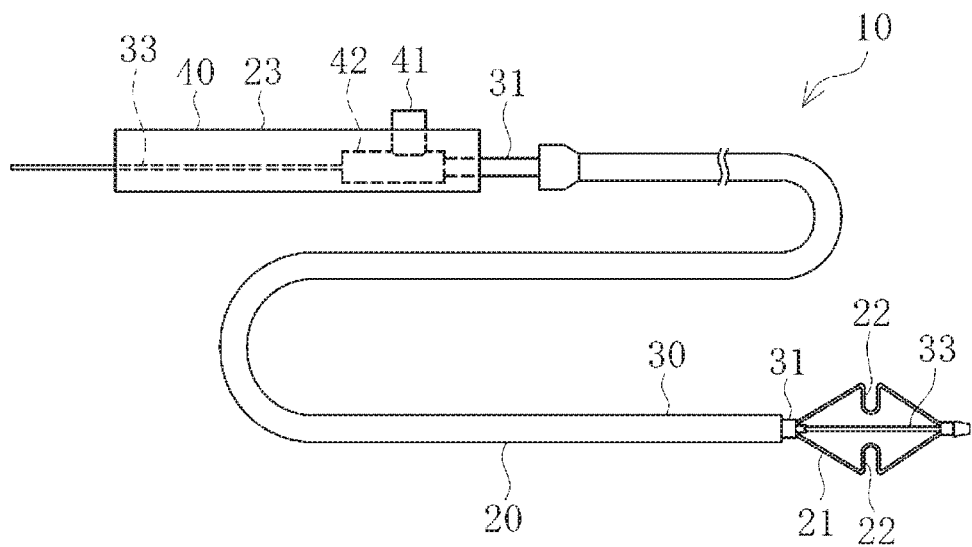
FIG. 1 is a front view illustrating an overall configuration of a medical device having an expansion body according to a first exemplary embodiment.

Set forth below with reference to the accompanying drawings is a detailed description of embodiments of a medical device including a maintenance treatment element which applies energy to a biological tissue representing examples of the inventive medical device. Note that since embodiments described below are preferred specific examples of the present disclosure, although various technically preferable limitations are given, the scope of the present disclosure is not limited to the embodiments unless otherwise specified in the following descriptions. In some cases, dimensional ratios in the drawings may be exaggerated and different from actual ratios for convenience of description. In addition, in the present specification, a side on which a medical device 10 is inserted into a biological lumen will be referred to as a "distal end" or a "distal side", and an operating hand-side will be referred to as a "proximal end" or a "proximal side".

The medical device 10 according to the embodiments described in this disclose may be configured as follows. A through-hole Hh formed in an atrial septum HA of a patient's heart H is enlarged, and further, a maintenance treatment is performed so that the through-hole Hh having an increased diameter is maintained to have an increased size.

As illustrated in FIG. 1, the medical device 10 according to the present embodiment includes an elongated shaft portion 20, an expansion body 21 disposed in a distal portion of the shaft portion 20, and an operation unit 23 disposed in a proximal portion of the shaft portion 20. The expansion body 21 has a maintenance treatment element (energy transfer element) 22 for performing the above-described maintenance treatment.

The shaft portion 20 has an outer shaft 31 that holds the expansion body 21 in the distal portion, and a storage sheath 30 that stores the outer shaft 31. The storage sheath 30 is movable forward and rearward from the outer shaft 31 in an axial direction. In a state where the storage sheath 30 is moved to the distal side of the shaft portion 20, the storage sheath 30 can internally store the expansion body 21. In a state where the expansion body 21 is stored, the storage sheath 30 is moved to the proximal side. In this manner, the expansion body 21 can be exposed.

A pulling shaft 33 is stored inside the outer shaft 31. The pulling shaft 33 projects from the distal end to the distal side of the outer shaft 31, and a distal portion of the pulling shaft 33 is fixed to a distal member 35. A proximal portion of the pulling shaft 33 is drawn out (i.e., extends) to the proximal side of the operation unit 23. The distal portion of the pulling shaft 33 is fixed is fixed to the distal member 35. The distal member 35 may not be fixed to the expansion body 21. In this manner, the distal member 35 can pull the expansion body 21 in a contracting direction. In addition, when the expansion body 21 is stored in the storage sheath 30, the distal member 35 is separated to the distal side from the expansion body 21. Accordingly, the expansion body 21 can be rather easily moved in an axial direction, and storage capability can be improved.

The operation unit 23 has a housing 40 configured to be held by an operator, an operation dial 41 that can be rotationally operated by the operator, and a conversion mechanism 42 operated in conjunction with the rotation of the operation dial 41. The pulling shaft 33 is held inside the operation unit 23 by the conversion mechanism 42. In conjunction with the rotation of the operation dial 41, the conversion mechanism 42 can move the held pulling shaft 33 forward and backward along the axial direction. For example, a rack and pinion mechanism can be used as the conversion mechanism 42.

Figure 2:
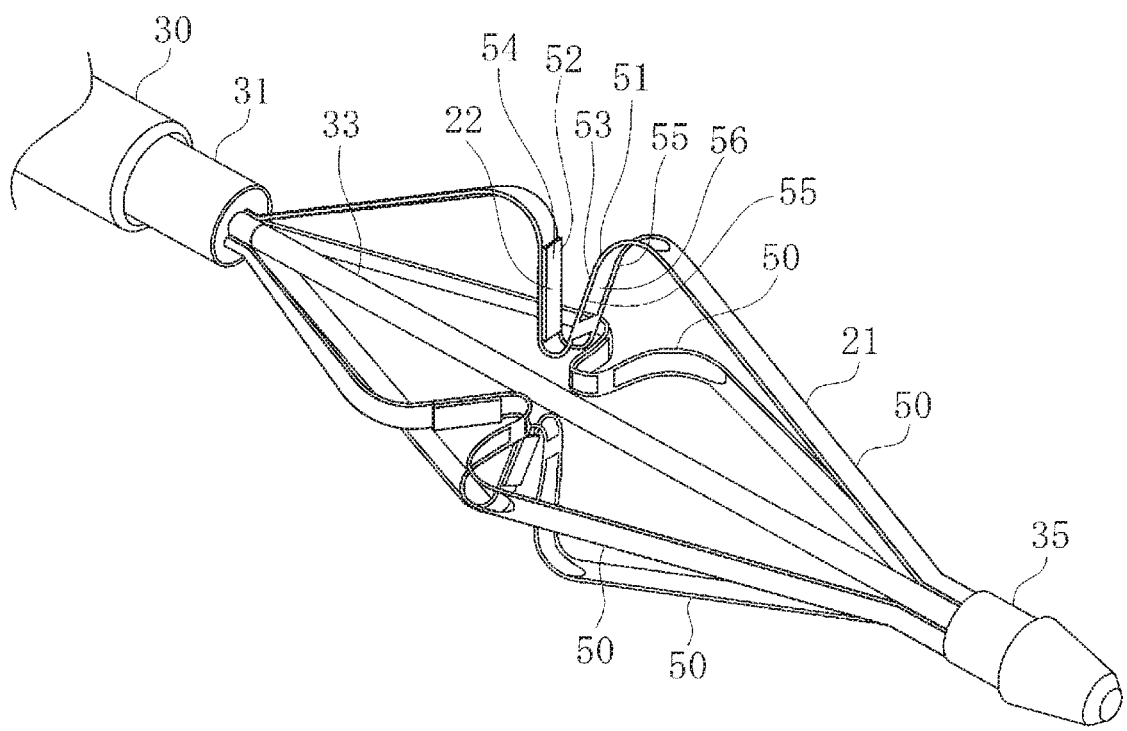
FIG. 2 is an enlarged perspective view illustrating the vicinity of the expansion body.

The expansion body 21 will be described in more detail. As illustrated in FIGS. 2 and 3, the expansion body 21 has a plurality of wire portions 50 in a circumferential direction. In the present embodiment, for example, four of the wire portions 50 are disposed in the circumferential direction.

The wire portions 50 are respectively configured to expand and contract in a radial direction. A proximal portion of the wire portion 50 extends from a distal portion to a distal side of the outer shaft 31. A distal portion of the wire portion 50 extends from a proximal portion to a proximal side of the distal member 35. The wire portion 50 is inclined to increase in the radial direction from both end portions toward a central portion in an axial direction. In addition, in the wire portion 50, the central portion in the axial direction has a holding portion 51 having a valley shape in the radial direction of the expansion body 21.

The holding portion 51 has a proximal side holding portion 52 and a distal side holding portion 53. The proximal side holding portion 52 has a projection portion 54 projecting toward the distal side. A maintenance treatment element 22 is disposed in the projection portion 54. In the distal side holding portion 53, a central portion in a width direction has a slit shape. The distal side holding portion 53 has an arm portion 55 on both sides and a hole portion 56 (i.e., hollow space) of the central portion.

As illustrated in FIG. 4A, the projection portion 54 of the proximal side holding portion 52 faces the hole portion 56 of the distal side holding portion 53 in the axial direction of the expansion body 21, which is a direction of holding the biological tissue. As illustrated in FIG. 4B, when the proximal side holding portion 52 and the distal side holding portion 53 are close to each other, the projection portion 54 can be fitted into the hole portion 56. In this way, in the direction of holding the biological tissue, a space-shaped region which the proximal side holding portion 52 or the distal side holding portion 53 can enter will be referred to as an opening portion 57.

The opening portion 57 may have or may not have a surface of the wire portion 50 outside the space region which the proximal side holding portion 52 can enter. In exemplary examples illustrated in FIGS. 2 to 4B, the opening portion 57 does not have the surface of the wire portion 50 outside the space region.

The distal side holding portion 53 has the opening portion 57 with respect to the proximal side holding portion 52, thereby forming an uneven structure between the proximal side holding portion 52 and the distal side holding portion 53. In this manner, when the biological tissue is held by the holding portion 51, the proximal side holding portion 52 and the distal side holding portion 53 support each other in the circumferential direction of the expansion body 21. Accordingly, both of the proximal side holding portion 52 and the distal side holding portion 53 can suppress positional displacement of the expansion body 21 in the circumferential direction. Therefore, an expansion force of the expansion body 21 can be reliably transmitted to the biological tissue. The proximal side holding portion 52 and the distal side holding portion 53 grip the biological tissue when the expansion body 21 expands. A time at which the expansion body 21 expands indicates any time of a period while the expansion body 21 expands, a moment when the expansion body 21 completely expands, and a period until the expansion body 21 contracts after completely expanding. In addition, in a case where the expansion body 21 expands in a state where the expansion body 21 is not inserted into a living body as illustrated in FIG. 2, at least one of the proximal side holding portion 52 and the distal side holding portion 53 (proximal side holding portion 52 in the present embodiment) faces the opening portion 57 at any time of the period while the expansion body 21 expands, the moment when the expansion body 21 completely expands, and the period until the expansion body 21 contracts after completely expanding.

Figure 5A:
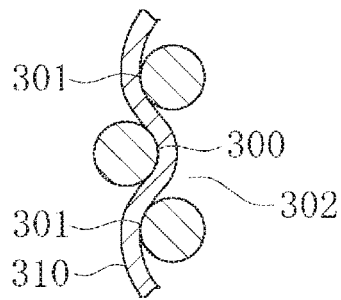
FIGS. 5A-5D are conceptual sectional views of a holding portion and a biological tissue which illustrates a pattern for holding the biological tissue between the proximal side holding portion and a distal side surface portion, and is a sectional view when a pulling shaft side is viewed from a holding portion.
Figure 5B:
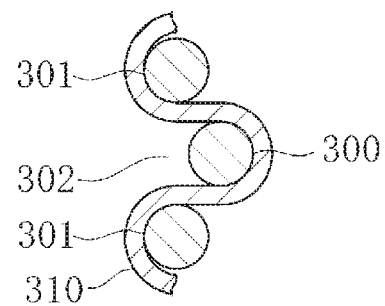

The uneven structure formed between the proximal side holding portion and the distal side holding portion will be described in more detail. FIGS. 5A-5D conceptually illustrate a proximal side holding portion 300, a distal side holding portion 301, and a biological tissue 310. The wire having the proximal side holding portion 300 and the distal side holding portion 301 is illustrated using a circular shape in a cross section for convenience of illustration. As a first pattern for holding the biological tissue by using the proximal side holding portion 300 and the distal side holding portion 301, it is conceivable to adopt a mode as follows. As illustrated in FIG. 5A, the biological tissue 310 deforms by being pinched between the proximal side holding portion 300 and the distal side holding portion 301, and the proximal side holding portion 300 enters the inside of the opening portion 302 formed between the proximal side holding portion 300 and the distal side holding portion 301. In addition, as a second pattern for holding the biological tissue by using the proximal side holding portion 300 and the distal side holding portion 301, it is also conceivable to adopt a mode as follows. As illustrated in FIG. 5B, the biological tissue 310 deforms by being pinched between the proximal side holding portion 300 and the distal side holding portion 301, and the proximal side holding portion 300 enters and penetrates the opening portion 302 formed between the proximal side holding portion 300 and the distal side holding portion 301. In any case, the opening portion 302 which the proximal side holding portion 300 can enter is formed. In this manner, it is possible to adopt a configuration in which the wire having the proximal side holding portion 300 and the wire having the distal side holding portion 301 are less likely to be displaced from each other in the width direction.

Figure 5C:
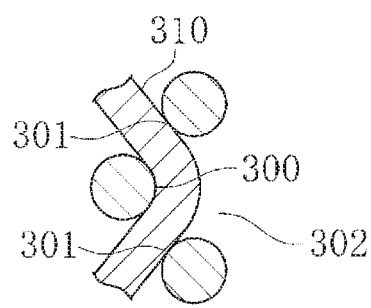
Figure 5D:
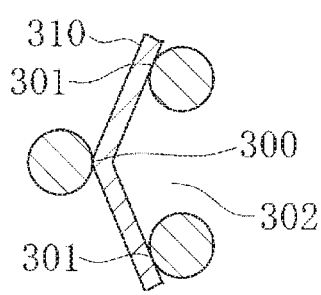

In addition, as third and fourth patterns for holding the biological tissue by using the proximal side holding portion 300 and the distal side holding portion 301, it is conceivable to adopt a mode as follows. As illustrated in FIGS. 5C and 5D, while the proximal side holding portion 300 faces the opening portion 302 formed between the proximal side holding portion 300 and the distal side holding portion 301, the proximal side holding portion 300 does not enter the opening portion 302. These modes may be adopted in a case where the biological tissue 310 is hard and less likely to deform, or in a case where the biological tissue 310 is relatively thick. In this case, the proximal side holding portion 300 does not actually enter the opening portion 302. However, the proximal side holding portion 300 faces the opening portion 302 in the direction of holding the biological tissue 310. Accordingly, it is possible to adopt a configuration in which the wire having the proximal side holding portion 300 and the wire having the distal side holding portion 301 are less likely to be displaced from each other in the width direction.

In this way, in any pattern of holding the biological tissue by using the proximal side holding portion 300 and the distal side holding portion 301, the uneven structure which enables the proximal side holding portion 300 to enter the opening portion 302 is formed. Accordingly, the positional displacement between the wires is prevented. In addition, in these patterns, the proximal side holding portion 300 and the distal side holding portion 301 are alternately located in the circumferential direction of the expansion body 21, thereby forming the uneven structure. Here, the patterns include a case where the proximal side holding portion 300 and the distal side holding portion 301 which are alternately located in the circumferential direction of the expansion body 21 are separated in the direction of holding the biological tissue.

In the present embodiment, the projection portion 54 is disposed in the proximal side holding portion 52, the opening portion 57 is disposed in the distal side holding portion 53, respectively. However, the projection portion 54 may be disposed in the distal side holding portion 53, and the opening portion 57 may be disposed in the proximal side holding portion 52, respectively.

For example, the wire portion 50 forming the expansion body 21 has a flat plate shape cut out from a cylinder. The wire forming the expansion body 21 can have, for example, a thickness of 50 µm to 500 µm and a width of 0.3 mm to 2.0 mm. However, the wire may have a dimension outside this range. In addition, the wire portion 50 may have a circular shape in a cross section, or may have other shapes in a cross section.

The maintenance treatment element 22 is disposed in the projection portion 54 of the proximal side holding portion 52. Accordingly, when the holding portion 51 grips (or pinches) the atrial septum HA, the energy from the maintenance treatment element 22 may be transferred to the atrial septum HA from the right atrium side.

For example, the maintenance treatment element 22 is configured to include a bipolar electrode that receives electric energy from an energy supply device (not illustrated) serving as an external device. In this case, electricity is supplied to the maintenance treatment element 22 disposed in each of the wire portions 50. The maintenance treatment element 22 and the energy supply device are connected to each other by a conducting wire (not illustrated) coated with an insulating coating material. The conducting wire is drawn outward (i.e., extends) via the shaft portion 20 and the operation unit 23, and is connected to the energy supply device.

Alternatively, the maintenance treatment element 22 may be configured to serve as a monopolar electrode. In this case, the electricity is supplied from a counter electrode plate prepared outside a body. In addition, the maintenance treatment element 22 may be a heating element (electrode chip) that generates heat by receiving high-frequency electric energy from the energy supply device. In this case, the electricity is supplied to the maintenance treatment element 22 disposed in each of the wire portions 50. Furthermore, the maintenance treatment element 22 can be configured to include an energy transfer element that applies energy to the through-hole Hh, such as a heater including an electric wire which provides heating and cooling operation or generating frictional heat by using microwave energy, ultrasound energy, coherent light such as laser, a heated fluid, a cooled fluid, or a chemical medium. A specific form of the energy transfer element is not particularly limited.

The wire portion 50 can be formed of a metal material. For example, the metal material of the wire portion 50 can be a titanium-based (Ti—Ni, Ti—Pd, or Ti—Nb—Sn) alloy, a copper-based alloy, stainless steel, β-titanium steel, or a Co—Cr alloy. An alloy having a spring property such as a nickel titanium alloy may also be used as the material of the wire portion. However, a material of the wire portion 50 is not limited, and the wire portion 50 may be formed of other materials.

The shaft portion 20 has an inner shaft 32 inside the outer shaft 31, and the pulling shaft 33 is stored inside the inner shaft 32. A guide wire lumen is formed in the pulling shaft 33 and the distal member 35 along the axial direction, and a guide wire 11 can be inserted into the guide wire lumen.

It is preferable that the storage sheath 30, the outer shaft 31, and the inner shaft 32 of the shaft portion 20 are formed of a material having a certain degree of flexibility. For example, the materials of the storage sheath 30, the outer shaft 31, and the inner shaft 32 of the shaft portion 20 may include polyolefin such as polyethylene, polypropylene, polybutene, ethylene-propylene copolymer, ethylene-vinyl acetate copolymer, ionomer, and a mixture of the above-described two or more materials, fluororesin such as soft polyvinyl chloride resin, polyamide, polyamide elastomer, polyester, polyester elastomer, polyurethane, and polytetrafluoroethylene, polyimide, PEEK, silicone rubber, or latex rubber.

For example, the pulling shaft 33 can be formed of the materials in which an elongated wire formed of a super elastic alloy such as a nickel-titanium alloy and a copper-zinc alloy, a metal material such as stainless steel, or a resin material having relatively high rigidity is coated with a resin material such as polyvinyl chloride, polyethylene, polypropylene, and ethylene-propylene copolymer.

For example, the distal member 35 can be formed of a polymer material such as polyolefin, polyvinyl chloride, polyamide, polyamide elastomer, polyurethane, polyurethane elastomer, polyimide, and fluororesin or a mixture of polymer materials. Alternatively, the distal member 35 can be formed of a multilayer tube containing two or more polymer materials.

Figure 7:
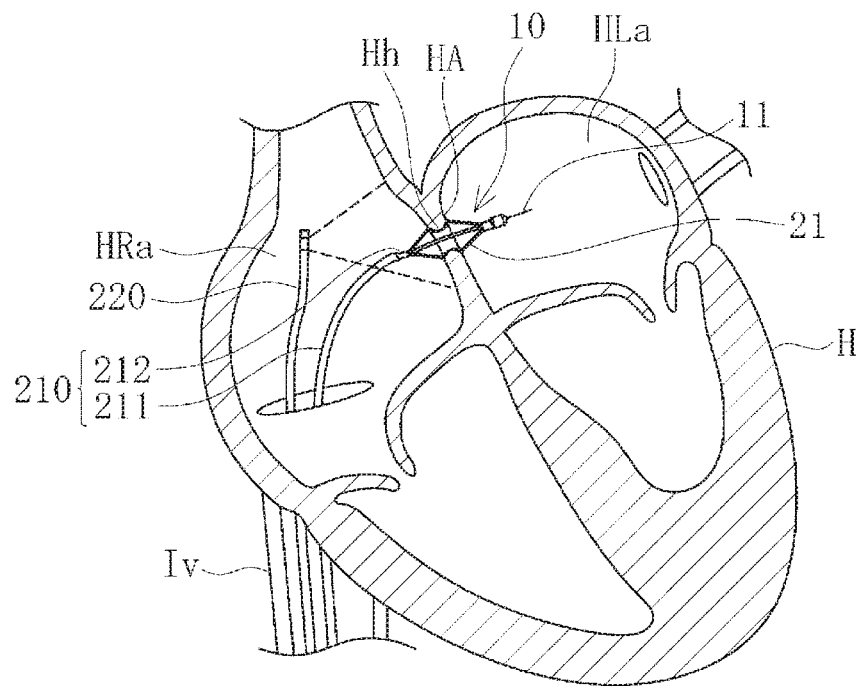
FIG. 7 is a view for describing the treatment method according to the present embodiment, and is a view for schematically describing a state where the expansion body is disposed in a through-hole of an atrial septum, in which the medical device is illustrated in a front view and the biological tissue is illustrated in a sectional view, respectively.

A treatment method using the medical device 10 will be described. The treatment method according to the present embodiment is performed on a patient suffering from a heart failure (left heart failure). More specifically, as illustrated in FIG. 7, the treatment method is performed on the patient suffering from a chronic heart failure, who has high blood pressure in a left atrium HLa due to myocardial hypertrophy appearing in a left ventricle of the heart H and increased stiffness (hardness).

As illustrated in FIG. 6, the treatment method according to the present embodiment includes forming the through-hole Hh in the atrial septum HA (S1), disposing the expansion body 21 in the through-hole Hh (S2), enlarging the diameter of the through-hole Hh by using the expansion body 21 (S3), confirming hemodynamics in the vicinity of the through-hole Hh (S4), performing the maintenance treatment for maintaining the size of the through-hole Hh (S5), and confirming the hemodynamics in the vicinity of the through-hole Hh after the maintenance treatment is performed (S6).

When the through-hole Hh is formed, an operator delivers an introducer 210 in which a guiding sheath 211 and a dilator 212 are combined with each other, to the vicinity of the atrial septum HA. For example, the introducer 210 can be delivered to a right atrium HRa via an inferior vena cava Iv. In addition, the introducer 210 can be delivered using the guide wire 11. The operator can insert the guide wire 11 into the dilator 212, and can deliver the introducer 210 along the guide wire 11. The introducer 210 and the guide wire 11 can be inserted into a living body by using a known method such as using a blood vessel introducer.

In the forming of the through-hole Hh in the atrial septum HA (S1), the operator causes a puncture device (not illustrated) to penetrate from the right atrium HRa side toward the left atrium HLa side, thereby forming the through-hole Hh. For example, a device such as a wire having a sharp distal end can be used as the puncture device. The puncture device is inserted into the dilator 212, and is delivered to the atrial septum HA. The puncture device can be delivered to the atrial septum HA instead of the guide wire 11 after the guide wire 11 is removed from the dilator 212.

In the enlarging of the diameter of the through-hole Hh by using the expansion body 21 (S2), the medical device 10 is first delivered to the vicinity of the atrial septum HA along the guide wire 11 inserted in advance. At this time, the distal portion of the medical device 10 penetrates the atrial septum HA, and reaches the left atrium HLa. In addition, when the medical device 10 is inserted, the expansion body 21 is in a state of being stored in the storage sheath 30.

Figure 8:
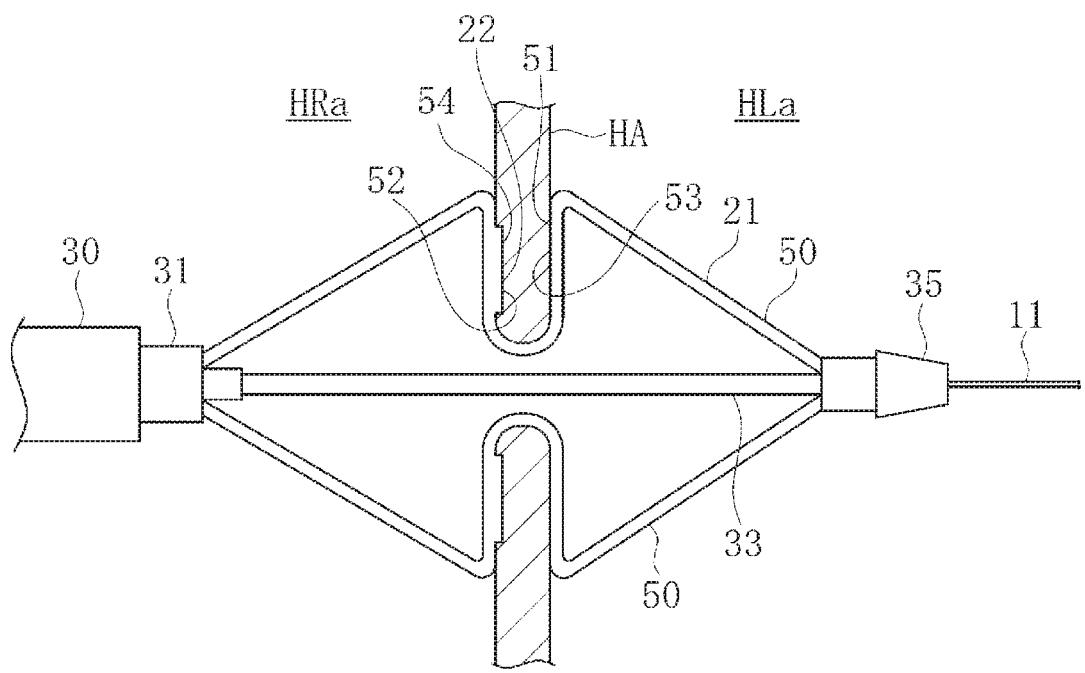
FIG. 8 is a view for schematically describing a state where the expansion body is disposed in the atrial septum, in which the medical device is illustrated in a front view and the biological tissue is illustrated in a sectional view, respectively.

Next, as illustrated in FIG. 8, the storage sheath 30 is moved to the proximal side so that the expansion body 21 is exposed. In this manner, the diameter of the expansion body 21 increases, and the holding portion 51 grips the atrial septum HA. At this time, the atrial septum HA is held by the proximal side holding portion 52 and the distal side holding portion 53. As described above, in the direction of holding the biological tissue, the proximal side holding portion 52 and the opening portion 57 face each other. Accordingly, a force acts so that the proximal side holding portion 52 and the distal side holding portion 53 support each other in the circumferential direction of the expansion body 21. Therefore, it is possible to suppress the torsion of the expansion body 21.

Figure 9:
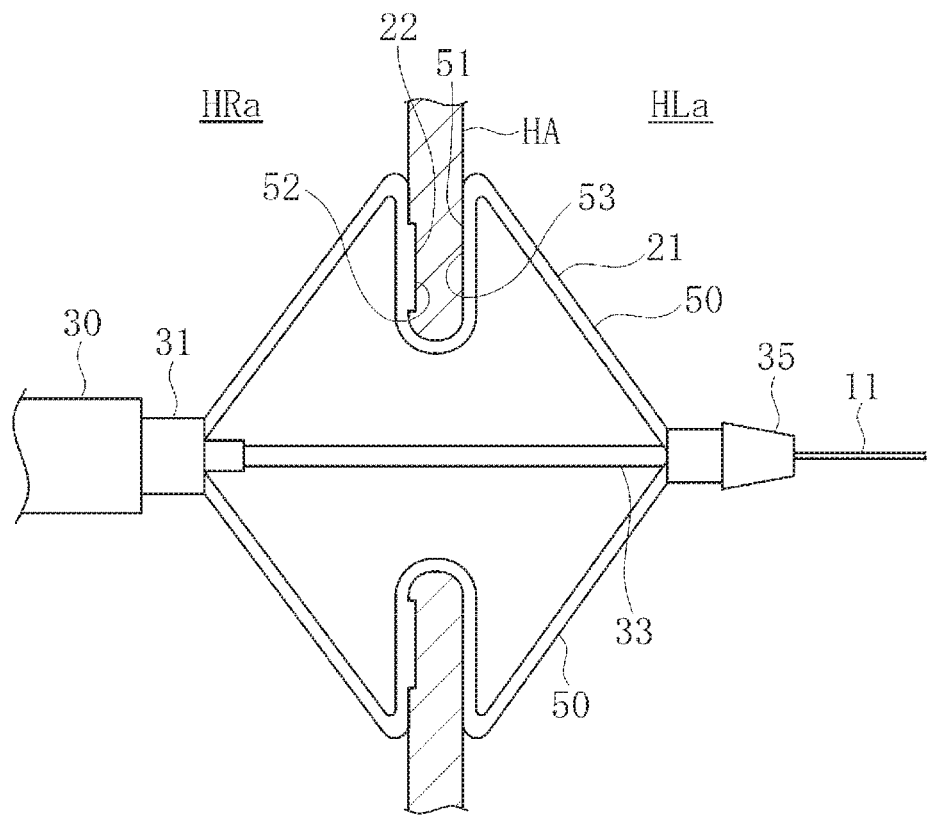
FIG. 9 is a view for schematically describing a state where a diameter of the expansion body is increased in the atrial septum, in which the medical device is illustrated in a front view and the biological tissue is illustrated in a sectional view, respectively.

In the enlarging of the diameter of the through-hole Hh by using the expansion body 21 (S3), the operator operates the operation unit 23 in a state where the holding portion 51 grips the atrial septum HA, and the pulling shaft 33 is moved to the proximal side. In this manner, as illustrated in FIG. 9, the expansion body 21 further expands in the radial direction, and the held through-hole Hh is widened in the radial direction. In this case, the torsion of the expansion body 21 is also suppressed. Accordingly, the expansion force can be reliably transmitted to the atrial septum HA.

After the through-hole Hh is enlarged, the hemodynamics is confirmed in the vicinity of the through-hole Hh (S4). As illustrated in FIG. 7, the operator delivers a hemodynamics confirming device 220 to the right atrium HRa by way of the inferior vena cava Iv. For example, a known echo catheter can be used as the hemodynamics confirming device 220. The operator can display an echo image acquired by the hemodynamics confirming device 220 on a display apparatus such as a display, and can confirm a blood volume passing through the through-hole Hh, based on a result of the echo image.

Next, the operator performs the maintenance treatment for maintaining the size of the through-hole Hh (S5). In the maintenance treatment, high-frequency energy is applied to an edge portion of the through-hole Hh through the maintenance treatment element 22, thereby cauterizing (heating and cauterizing) the edge portion of the through-hole Hh by using the high-frequency energy. When the biological tissue in the vicinity of the edge portion of the through-hole Hh is cauterized through the maintenance treatment element 22, a degenerated portion having the degenerated biological tissue is formed in the vicinity of the edge portion. The biological tissue in the degenerated portion is in a state where elasticity is lost. Accordingly, the through-hole Hh can maintain a shape widened by the expansion body 21.

The maintenance treatment element 22 is disposed in the projection portion 54 of the proximal side holding portion 52. Therefore, the projection portion 54 is pressed against the atrial septum HA. In this manner, the maintenance treatment is performed in a state where the maintenance treatment element 22 is incorporated in the biological tissue. In this manner, the maintenance treatment element 22 is prevented from coming into contact with the blood during the maintenance treatment. Accordingly, it is possible to suppress appearance of a thrombus caused by a current leaking into the blood.

After the maintenance treatment is performed, the hemodynamics are confirmed again in the vicinity of the through-hole Hh after the maintenance treatment (S6). In a case where the blood volume passing through the through-hole Hh reaches a desired volume, the operator decreases the diameter of the expansion body 21. After the expansion body 21 is stored in the storage sheath 30, the expansion body 21 is removed from the through-hole Hh. Furthermore, the whole medical device 10 is removed outward of the living body, and the treatment is completed.

Figure 10:
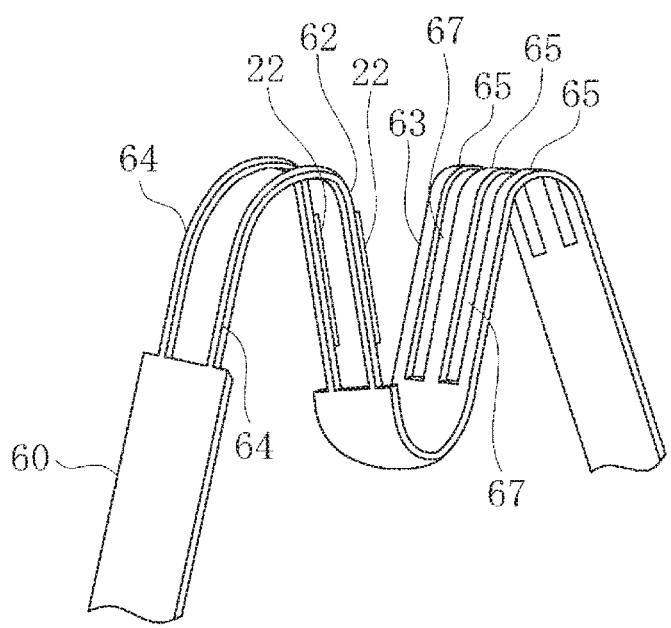
FIG. 10 is an enlarged perspective view illustrating the vicinity of a holding portion of a wire portion according to a first modification example.

A modification example of the wire portion will be described. As illustrated in FIG. 10, a wire portion 60 has two proximal side arm portions 64 and three distal side arm portions 65. A distal side surface of the proximal side arm portion 64 is a proximal side holding portion 62 that grips the biological tissue, and the maintenance treatment element 22 is disposed in the proximal side holding portion 62. In addition, a proximal side surface of the distal side arm portion 65 is a distal side holding portion 63 that grips the biological tissue. An opening portion 67 is formed between the distal side arm portions 65. The proximal side arm portion 64 and the distal side arm portion 65 are formed not to overlap each other in the width direction of the wire portion 60. Therefore, the proximal side holding portion 62 faces the opening portion 67 formed between the distal side arm portions 65 in the direction of holding the biological tissue. In this way, more arm portions may be formed in the wire portion 60. In this manner, a plurality of the uneven structures of the proximal side holding portion 62 and the opening portion 67 may be formed in the width direction of the wire portion 60.

Figure 11:
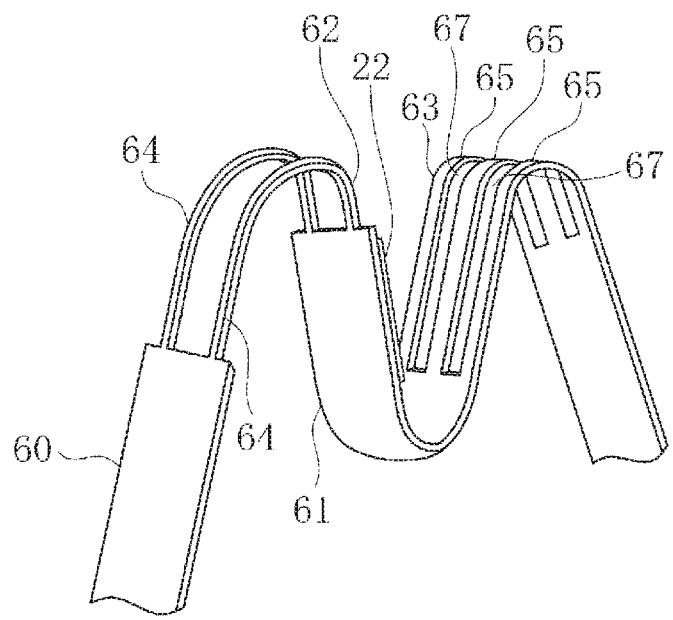
FIG. 11 is an enlarged perspective view illustrating the vicinity of a holding portion of a wire portion according to a second modification example.

As illustrated in FIG. 11, in the wire portion 60, a portion having the maintenance treatment element 22 may be formed in a flat shape, and a plurality of the proximal side arm portions 64 may be formed in the proximal side portion from the maintenance treatment element 22. In this case, the proximal side holding portion 62 of the proximal side arm portion 64 and the opening portion 67 which the proximal side holding portion 62 can enter are formed on an upper portion of the holding portion 61. In addition, an arm portion 68 may be further formed in a lower portion of the region having the maintenance treatment element 22. In this manner, it is possible to adopt a configuration in which the holding portion 61 is likely to deform to easily grip the biological tissue. In addition, a surface for disposing the maintenance treatment element 22 may be formed between the proximal side arm portions 64. In addition, while a surface for disposing the maintenance treatment element 22 is formed between the proximal side arm portions 64, the arm portion 68 may be formed in the lower portion of the region.

Figure 12A:
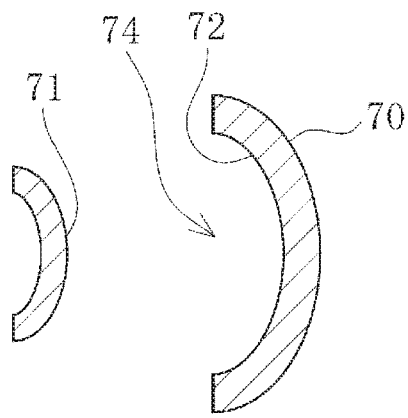
FIG. 12A is a sectional view of a holding portion of a wire portion in a case where a distal side surface portion of the wire portion according to a third modification example has a recessed shape.
Figure 12B:
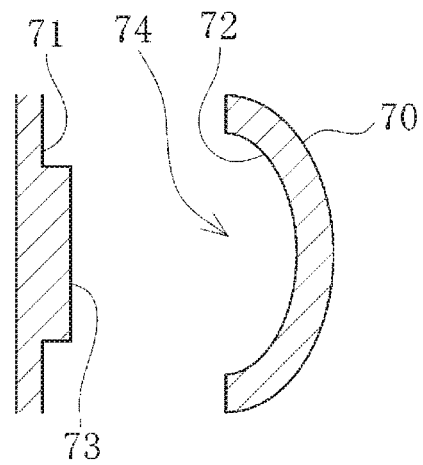
FIG. 12B is a sectional view when a pulling shaft side is viewed from the holding portion.

As illustrated in FIGS. 12A and 12B, the wire portion 70 may have an arcuate shape in a cross section, and the distal side holding portion 72 may have an opening portion 74 recessed toward the proximal side. In this case, as illustrated in FIG. 12A, a proximal side holding portion 71 also has an arcuate shape in a cross section. Accordingly, it is possible to form a projection portion 73 that can enter the opening portion 74. In addition, as illustrated in FIG. 12B, the distal side holding portion 72 may be formed to have an arcuate shape in a cross section, and the opening portion 74 may be formed as in the case illustrated in FIG. 12A. The proximal side holding portion 71 may be formed in a flat plate shape as in FIG. 3, and the projection portion 73 that can enter the opening portion 74 may be formed. In these cases, when the expansion body 21 expands, the proximal side holding portion 71 and the distal side holding portion 72 have a structure in which both of these are fitted together.

Figure 13:
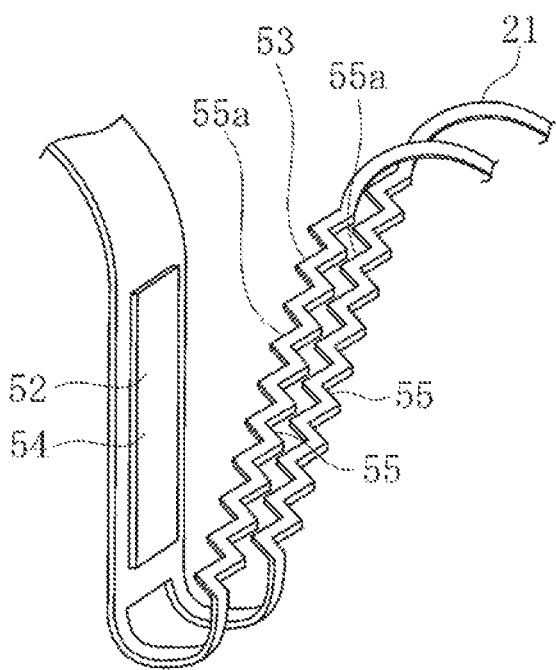
FIG. 13 is an enlarged perspective view illustrating the vicinity of a holding portion of a wire portion in which a distal side surface portion of the wire portion according to a fourth modification example has a serrate portion.

As illustrated in FIG. 13, the arm portion 55 formed in the distal side holding portion 53 may have a serrate portion 55a having a shape in which a fine mountain shape and a valley shape are repeated. In this manner, when the proximal side holding portion 52 and the distal side holding portion 53 grip the atrial septum HA, the serrate portion 55a functions as a slip stopper. Both of these are much less likely to be displaced from each other, and it is possible to further suppress the torsion of the expansion body 21 in the circumferential direction.

Figure 14:
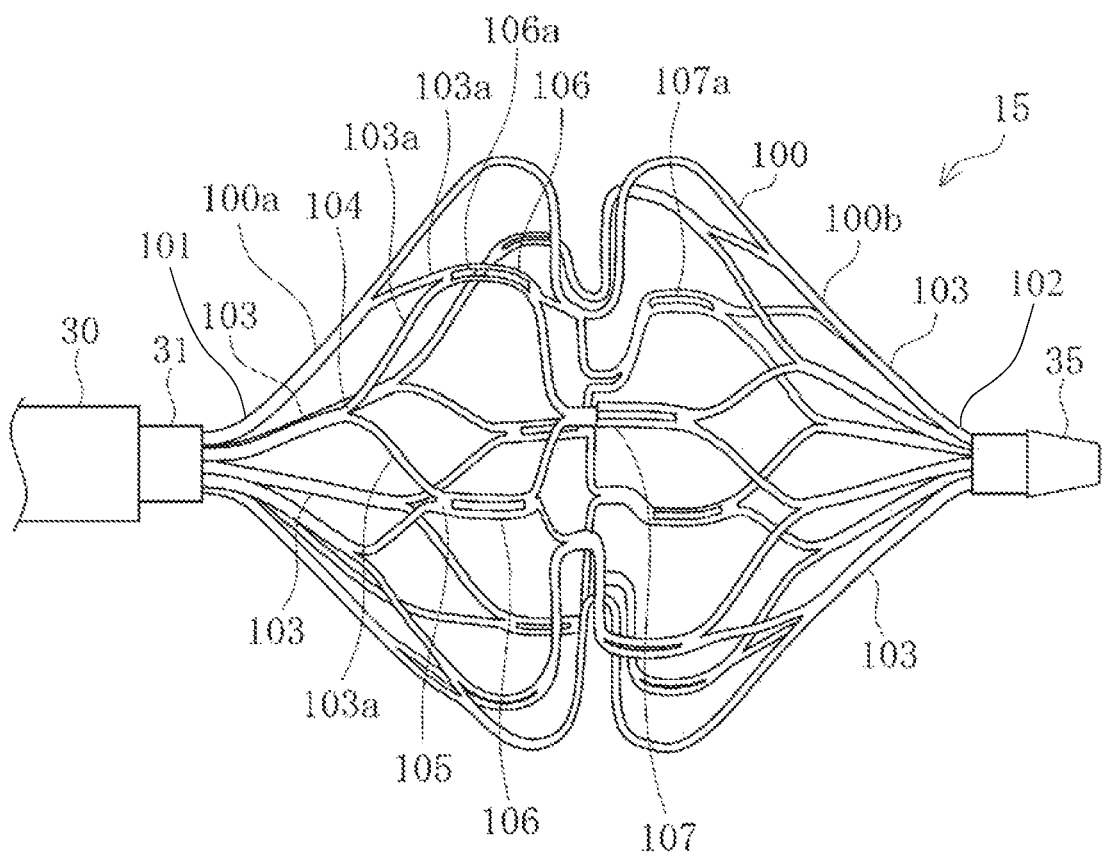
FIG. 14 is an enlarged front view illustrating the vicinity of an expansion body in a medical device according to a second exemplary embodiment.

Next, a medical device 15 according to a second exemplary embodiment will be described. A configuration of the medical device 15 according to the present embodiment is the same as that according to the first exemplary embodiment except for an expansion body 100, and thus, description of the medical device 15 will be omitted. As illustrated in FIG. 14, the expansion body 100 has a plurality of wire portions 103 in the circumferential direction. The wire portion 103 extends from the distal portion of the outer shaft 31 toward the distal side of the outer shaft 31, and extends from the proximal portion of the distal member 35 toward the proximal side.

The wire portion 103 extending from a proximal portion 101 toward the distal side has an inclined shape that expands in the radial direction, and an intermediate portion of the wire portion 103 has a bifurcated portion 104 bifurcated into two lines. The bifurcated line 103a bifurcated in the bifurcated portion 104 merges with a bifurcated line 103a extending from the adjacent wire portion 103 in a merging portion 105. The wire portion 103 is linked with the wire portion 103 adjacent in the circumferential direction by the bifurcated line 103a. A proximal side holding portion 106 is formed on the distal side from the merging portion 105. The proximal side holding portion 106 is a portion of the wire portion 103 where the two bifurcated lines 103a and 103a merge with each other. In the expansion body 100, a portion from the proximal portion 101 to the proximal side holding portion 106 is a proximal side expansion portion 100a. The wire portion 103 extending from a distal portion 102 toward the proximal side has a symmetrical shape with the wire portion 103 extending from the proximal portion 101 toward the distal side with respect to a plane orthogonal to the axial direction of the expansion body 100 which includes a center position in the axial direction of the expansion body 100, and is linked with the wire portion 103 adjacent in the circumferential direction by the bifurcated portion 104 and the merging portion 105. A distal side holding portion 107 is formed on the proximal side from the merging portion 105. The distal side holding portion 107 is a portion of the wire portion 103 where the two bifurcated lines 103a and 103a merge with each other. In the expansion body 100, a portion from the distal portion 102 to the distal side holding portion 107 is a distal side expansion portion 100b. Slit holes 106a and 107a are formed in the proximal side holding portion 106 and the distal side holding portion 107. The proximal side holding portion 106 and the distal side holding portion 107 are likely to be bent, and a central portion of the expansion body 100 is formed in a valley shape (i.e., V shape).

A circumferential position of the wire portion 103 extending from the proximal portion 101 to the distal side is different from a circumferential position of the wire portion 103 extending from the distal portion 102 to the proximal side. Therefore, when the expansion body 100 expands, the proximal side holding portion 106 and the distal side holding portion 107 are alternately located in the circumferential direction, thereby forming an uneven shape. In the central portion of the expansion body 100, the bifurcated line 103a is formed between the proximal side holding portion 106 and the distal side holding portion 107. The proximal side holding portion 106 and the distal side holding portion 107 which are disposed at different positions in the circumferential direction are linked with each other.

The wire portion 103 having this shape can be formed by performing laser cutting on a single metal cylindrical member.

Figure 15:
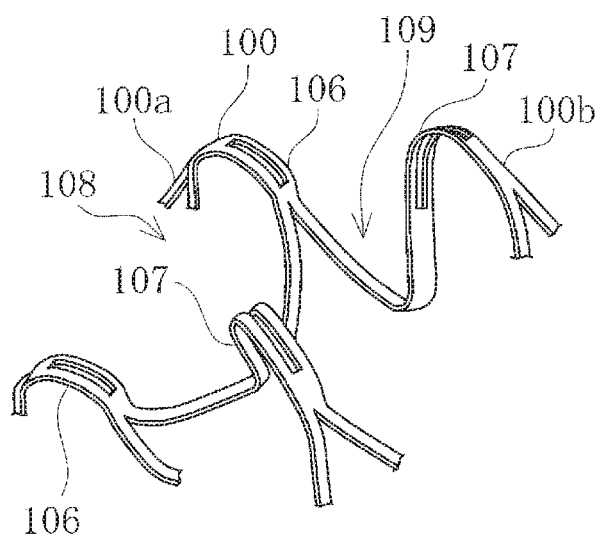
FIG. 15 is an enlarged perspective view illustrating a relationship between a proximal side holding portion and a distal side holding portion in the expansion body of the medical device according to the second exemplary embodiment.

As illustrated in FIG. 15, in the axial direction of the expansion body 100, the proximal side holding portion 106 faces a distal side opening portion 109 formed between the distal side holding portions 107 which are the wire portions 103 adjacent in the circumferential direction. In addition, in the axial direction of the expansion body 100, the distal side holding portion 107 faces a proximal side opening portion 108 formed between the proximal side holding portions 106 which are the wire portions 103 adjacent in the circumferential direction. In this manner, the uneven structure is formed between the proximal side holding portion 106 and the distal side holding portion 107. When the expansion body 100 expands in the radial direction, the uneven structure can suppress the torsion in the circumferential direction. In addition, as shown in FIG. 14, the wire portion 103 is linked with the adjacent wire portion 103 in the circumferential direction. Accordingly, it is also possible to suppress the torsion (i.e., twisting) of the wire portion 103 in the circumferential direction.

As described above, the medical device 10 according to the above-described embodiment includes the elongated shaft portion 20, and the expansion body 21 disposed in the distal portion of the shaft portion 20. The expansion body 21 has the wire portion 50 configured to expand and contract in the radial direction. The wire portion 50 has the proximal side holding portion 52 and the distal side holding portion 53 which grip the biological tissue. When the expansion body 21 expands, at least one surface portion of the proximal side holding portion 52 and the distal side holding portion 53 faces the opening portion 57. In this manner, in the medical device 10 according to the present embodiment, the proximal side holding portion 52 and the distal side holding portion 53 do not directly face each other in the axial direction of the expansion body 21. Accordingly, when the proximal side holding portion 52 and the distal side holding portion 53 grip the biological tissue, the positional displacement in the circumferential direction can be suppressed, and the torsion of the expansion body 21 in the circumferential direction can be suppressed. Therefore, the expansion force can be reliably transmitted to the biological tissue.

In addition, when the holding portion 51 has the valley shape in the radial direction of the expansion body 21, the uneven structure is formed between the proximal side holding portion 52 and the distal side holding portion 53 which face each other in the holding portion 51. Accordingly, when the expansion body 21 expands, the positional displacement between both of these can be suppressed, and the torsion of the expansion body 21 in the circumferential direction can be suppressed.

In addition, when the opening portion 57 is formed using the hole portion 56 of the wire portion 50, the opening portion 57 can be formed using a structure that is relatively easy to make.

In addition, when the opening portion 74 is formed in the recessed shape of the wire portion 70, the opening portion 74 can be formed using a structure that is relatively easy to make.

In addition, when the maintenance treatment element 22 is disposed in one of the proximal side holding portion 52 and the distal side holding portion 53, one of the proximal side holding portion 52 and the distal side holding portion 53 comes into pressing contact with the biological tissue. In this manner, the maintenance treatment element 22 can be prevented from being exposed to the blood, and appearance of a thrombus can be suppressed.

In addition, a plurality of the wire portions 103 are disposed in the circumferential direction of the expansion body 100. The proximal side expansion portion 100a having the proximal side holding portion 106 in the expansion body 100 has the proximal side opening portion 108 formed between the proximal side holding portions 106 adjacent in the circumferential direction and formed using the wire portion 103 where the bifurcated lines 103a and 103a merge with each other. The distal side expansion portion 109 having the distal side holding portion 107 in the expansion body 100 has the distal side opening portion 109 formed between the distal side holding portions 107 adjacent in the circumferential direction and formed using the wire portion 103 where the bifurcated lines 103a and 103a merge with each other. The proximal side holding portion 106 faces the distal side opening portion 109, and the distal side holding portion 107 faces the proximal side opening portion 108. In this case, the proximal side holding portion 106 and the distal side holding portion 107, respectively, face the distal side opening portion 109 and the proximal side opening portion 108, thereby suppressing the positional displacement. Therefore, it is possible to suppress the torsion of the expansion body 21 in the circumferential direction.

In addition, when the wire portion 103 is bifurcated into the bifurcated line 103a between the proximal side holding portion 106 and the distal side holding portion 107, and the proximal side holding portion 106 and the distal side holding portion 107 which are disposed at different positions in the circumferential direction are linked with each other in the bifurcated line 103a, the wire portions 103 are linked with each other in the circumferential direction. Therefore, it is possible to further suppress the torsion of the expansion body 100 in the circumferential direction.

In addition, the medical device 10 according to the above-described embodiment has the elongated shaft portion 20, and the expansion body 21 disposed in the distal portion of the shaft portion 20, and configured to expand and contract in the radial direction. The expansion body 21 has a plurality of the wire portions 50 linked with the shaft portion 20, and the proximal side holding portion 52 and the distal side holding portion 53 which are formed using at least one of the wire portions 50, and which grip the biological tissue. When the expansion body 21 expands, the proximal side holding portion 52 and the distal side holding portion 53 are fitted together, or are alternately located in the circumferential direction. In this manner, the proximal side holding portion 52 and the distal side holding portion 53 have a relationship in which both of these are fitted together or alternately located in the circumferential direction, thereby forming the uneven structure. The uneven structure suppresses the positional displacement in the circumferential direction when the biological tissue is held by the proximal side holding portion 52 and the distal side holding portion 53, and the torsion of the expansion body 21 in the circumferential direction is suppressed. Therefore, the expansion force can be reliably transmitted to the biological tissue.

The present disclosure is not limited to the above-described embodiments, and various modifications can be made by those skilled in the art within the technical idea of the present disclosure.

Figure 16:
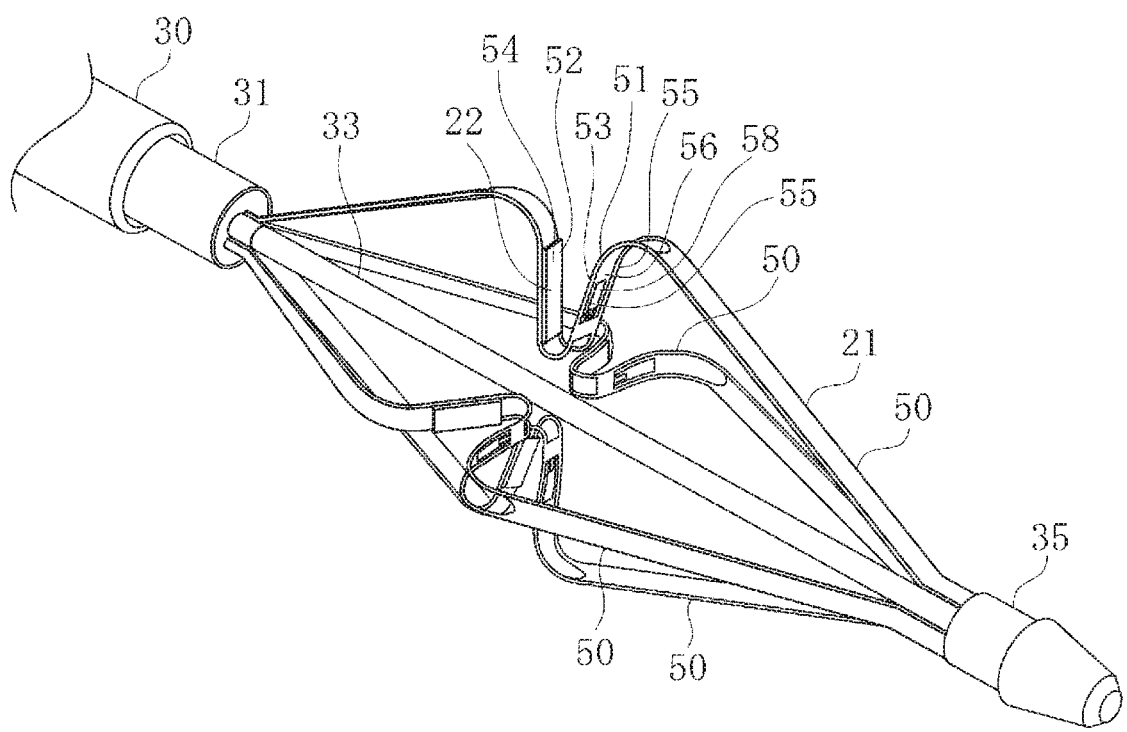
FIG. 16 is an enlarged perspective view illustrating the vicinity of a holding portion of a wire portion according to a fifth modification example.

For example, as a fifth modification example of the first exemplary embodiment, as illustrated in FIG. 16, the distal side holding portion 53 may have a support portion 58 that faces the maintenance treatment element 22 disposed in the projection portion 54. The support portion 58 protrudes toward an inner region surrounded by the hole portion 56 between the arm portions 55 disposed on both sides of the distal side holding portion 53. The support portion 58 is disposed away from the two arm portions 55 between the two arm portions 55, and protrudes substantially parallel to the two arm portions 55. When the proximal side holding portion 52 and the distal side holding portion 53 are close to each other, and the biological tissue is pinched between the proximal side holding portion 52 and the distal side holding portion 53, the maintenance treatment element 22 presses the biological tissue to the distal side. At this time, the biological tissue pressed by the maintenance treatment element 22 is supported by the support portion 58, and is suppressed not to escape to the distal side. Therefore, while the biological tissue is pinched by the uneven structure of the projection portion 54 and the hole portion 56, the biological tissue is pinched between the maintenance treatment element 22 and the support portion 58. At this time, the support portion 58 may be bent to a certain degree so that the biological tissue is rather easily pinched by the uneven structure of the projection portion 54 and the hole portion 56. As described above, the medical device 10 has the support portion 58. Accordingly, close contact between the maintenance treatment element 22 and the biological tissue may be improved.

The detailed description above describes embodiments of a medical device including a maintenance treatment element which applies energy to a biological tissue. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
an elongated shaft portion; and
an expansion body disposed in a distal portion of the shaft portion, the expansion body configured to expand and contract in a radial direction,
wherein the expansion body includes a plurality of wire portions linked with the shaft portion, and a holding portion is formed using at least one of the plurality of wire portions,
wherein at least one of a proximal side and a distal side of the holding portion includes an opening portion formed in a wire portion or formed using two or more of the plurality of wire portions, and the holding portion is configured to hold a biological tissue by the proximal side and the distal side of the holding portion, and
wherein the expansion body is configured to expand such that the wire portion forming the holding portion faces the opening portion in a direction of holding the biological tissue by the proximal side and the distal side of the holding portion.

2. The medical device according to claim 1,
wherein the holding portion has a valley shape in the radial direction of the expansion body, and
when the expansion body expands in the radial direction, one of the proximal side and the distal side of the holding portion faces the opening portion in the direction of holding the biological tissue with the holding portion being valley shape such that the holding portion holds a biological tissue between the proximal side and the distal side of the holding portion, and that the proximal side and the distal side of the holding portion support each other in a circumferential direction of the expansion body.

3. The medical device according to claim 2, wherein the opening portion is formed using a hole portion of the wire portion.

4. The medical device according to claim 2, wherein the opening portion is formed in a recessed shape of the wire portion.

5. The medical device according to claim 2, wherein a maintenance treatment element is disposed in the holding portion.

6. The medical device according to claim 1, wherein the plurality of wire portions are disposed in a circumferential direction of the expansion body.

7. The medical device according to claim 6, further comprising:
a proximal side expansion portion having proximal side holding portions in the expansion body has a proximal side opening portion formed between the proximal side holding portions adjacent to each other in a circumferential direction;
a distal side expansion portion having distal side holding portions in the expansion body has a distal side opening portion formed between the distal side holding portions adjacent to each other in the circumferential direction; and
wherein the proximal side holding portion faces the distal side opening portion, and the distal side holding portion faces the proximal side opening portion.

8. The medical device according to claim 7, wherein the wire portion is bifurcated into a bifurcated line between the proximal side holding portion and the distal side holding portion, and the proximal side holding portion and the distal side holding portion which are disposed at different positions in the circumferential direction are linked with each other in the bifurcated line.

9. A medical device comprising:
an elongated shaft portion; and
an expansion body disposed in a distal portion of the shaft portion, the expansion body configured to expand and contract in a radial direction,
wherein the expansion body including a plurality of wire portions linked with the shaft portion, and a proximal side holding portion and a distal side holding portion which are formed using at least one wire portion of the plurality of wire portions,
wherein the expansion body is configured to expand such that the proximal side holding portion and the distal side holding portion are alternately located in a circumferential direction of the expansion body.

10. The medical device according to claim 9, wherein a maintenance treatment element is disposed in one or more of the proximal side holding portion and the distal side holding portion.

11. The medical device according to claim 9, wherein the at least one wire portion is bifurcated into a bifurcated line between the proximal side holding portion and the distal side holding portion, and the proximal side holding portion and the distal side holding portion which are disposed at different positions in the circumferential direction are linked with each other in the bifurcated line.

12. A treatment method of enlarging a through-hole of a biological tissue by using a medical device having an expansion body configured to expand and contract in a radial direction, the method comprising:
positioning the expansion body with a holding portion in the through-hole of the biological tissue, the expansion body including a plurality of wire portions linked with the shaft portion, and the holding portion formed using at least one of the plurality of wire portions, and at least one of a proximal side and a distal side of the holding portion includes an opening portion formed in a wire portion or formed using two or more of the plurality of wire portions;
causing the holding portion to face the opening portion in a direction of holding the biological tissue by the proximal side and the distal side of the holding portion and to further hold the biological tissue from both sides of the through-hole by the proximal side and the distal side of the holding portion;
enlarging a diameter of the through-hole by expanding the expansion body; and
performing a maintenance treatment by using a maintenance treatment element of the holding portion.

13. The treatment method according to claim 12, further comprising:
performing the causing of the holding portion to hold the biological tissue before, after, or simultaneously with the enlarging of the diameter of the through-hole by expanding the expansion body.

14. The treatment method according to claim 12, further comprising:
forming a valley shape in the holding portion in the radial direction by the proximal side and the distal side of the holding portion and facing one of the proximal side and the distal side of the holding portion to the opening portion in the direction of holding the biological tissue so as to hold the biological tissue between the proximal side and the distal side of the holding portion and support the proximal side and the distal side of the holding portion each other in a circumferential direction of the expansion body.

15. The treatment method according to claim 12, wherein the holding portion has a valley shape in the radial direction of the expansion body, the method further comprising:
forming the opening portion using a hole portion of the wire portion.

16. The treatment method according to claim 15, further comprising:
forming the opening portion in a recessed shape of the wire portion.

17. The treatment method according to claim 12, further comprising:
disposing the maintenance treatment element in one or more of the proximal side and the distal side of the holding portion.

18. The treatment method according to claim 12, further comprising:
disposing the plurality of wire portions in a circumferential direction of the expansion body.

19. The treatment method according to claim 18, further comprising:

a proximal side expansion portion having proximal side holding portions in the expansion body has a proximal side opening portion formed between the proximal side holding portions adjacent to each other in a circumferential direction;

a distal side expansion portion having distal side holding portions in the expansion body has a distal side opening portion formed between the distal side holding portions adjacent to each other in the circumferential direction; and wherein the proximal side holding portion faces the distal side opening portion, and the distal side holding portion faces the proximal side opening portion.

20. The treatment method according to claim 19, further comprising:

bifurcating the wire portion into a bifurcated line between the proximal side holding portion and the distal side holding portion, and the proximal side holding portion and the distal side holding portion which are disposed at different positions in the circumferential direction are linked with each other in the bifurcated line.

* * * * *